United States Patent [19]
Lee

[11] Patent Number: 6,013,021
[45] Date of Patent: Jan. 11, 2000

[54] BIOFIELD VITALIZER

[76] Inventor: Richard H. Lee, 115 N. El Camino Real, San Clemente, Calif. 92672

[21] Appl. No.: 08/988,139

[22] Filed: Dec. 10, 1997

[51] Int. Cl.$^7$ ...................................................... A61N 2/00
[52] U.S. Cl. ................................................. 600/9; 600/15
[58] Field of Search ............................... 600/9–15; 96/26, 96/55, 48, 69, 80, 97, 98; 361/226, 235

[56] References Cited

U.S. PATENT DOCUMENTS

| | | | |
|---|---|---|---|
| 3,943,912 | 3/1976 | Nakayama | 600/15 |
| 4,095,587 | 6/1978 | Ishikawa | 600/15 |
| 5,351,389 | 10/1994 | Erickson et al. | 600/9 |
| 5,484,472 | 1/1996 | Weinberg . | |
| 5,782,743 | 7/1998 | Russell | 600/9 |

*Primary Examiner*—John P. Lacyk

[57] ABSTRACT

A biofield vitalizer offsets adverse effects of travel. A corona discharge air cleaner (12) produces high energy particles like ozone, nitric oxide, and free electrons to purify the air and provide electrical vitality to the passenger's body. A magnet (16) at the base of the cervical spine provides a magnetic field through the lungs and heart equivalent to that of Earth at ground level to supplement the available magnetic energy in the body. This magnetic field also pulls stagnant energy out of the base of the neck to reduce the buildup of tension in the neck, and in combination with the electric vitality, reduces the traveler's sensitivity to crowds. It may also be employed as an integral part of vehicles or spaces including chairs wherein the magnet is installed in the seat and an ionizer is installed in the space or in the ventilation system.

15 Claims, 2 Drawing Sheets

BIOFIELD VITALIZER

BACKGROUND—FIELD OF INVENTION

This invention relates to environmental conditioning devices, specifically to an electric and magnetic field generator for personal health and comfort during travel.

BACKGROUND—DISCUSSION OF PRIOR ART

Most air travelers experience exhaustion after a long flight, and some feel acute discomfort. My research indicates that the following are principal causes of health problems in modem aircraft: airborne pathogens and pollution, a reduced ambient magnetic field, reduced electrical energy in the air, and proximity to crowds of people.

Air ionizers and ozone generators of many designs and configurations are available, as are magnets in a wide variety of shapes and configurations for many purposes.

U.S. Pat. No. 5,484,472 to Weinberg (1996) describes a small battery-powered air purifier which can be worn around the neck. This device ionizes air and creates high energy particles like ozone which purify the air of pathogens. This purified air is then propelled upward toward the face so that the individual breathes purified air. While the Weinberg product purifies the air of pathogens and pollution and produces electrically energized air, it does not supplement the magnetic field available to the body, or to reduce the body's sensitivity to crowds. Also, it draws air from above, from the same air space to which it discharges, recycling purified air, and thus suffers from reduced efficiency.

And while many magnetic products are purported to relieve motion sickness, none include electrical ionization, provide a significant magnetic field beyond the surface layers of the body, or reduce the body's sensitivity to crowds.

OBJECTS AND ADVANTAGES

Accordingly, several other objects and advantages of the present invention are:

(a) to provide a device which overcomes the problems of exhaustion, discomfort, and exposure to pathogens which are common during air travel, (b) to provide a device which supplements the available electrical energy stored in the air surrounding an air traveler so as to provide a sufficient supply of this vital energy such that the traveler can continue to function normally during the flight without becoming exhausted.

Other objects and advantages are:

(a) to provide a field of magnetic energy through the heart and lungs which is equivalent in field strength to Earth's magnetic field at ground level so that the body can collect the required magnetic energy to prevent exhaustion and avoid the exacerbation of symptoms of rising heat, nausea, and anxiety which are common symptoms among some air travelers, (b) to provide removal of muscle tension and discomfort from the base of the neck by positioning the negative pole of the magnet to face this point, (c) to provide the constriction of the biofield surrounding the body, reducing psychic sensitivity for those who are highly sensitive to and uncomfortable with being in crowded group situations by means of both the increased electrical and magnetic material available to the body and the positioning of the magnet at the base of the neck, (d) to provide a large diameter, low strength magnet which produces a magnetic field at the center of the chest of field strength equivalent to Earth's magnetic field at ground level, without causing excessive field strength at the base of the neck which would make people with psychic sensitivity feel uncomfortable.

DRAWING FIGURES

Other objects and advantages will become apparent from a consideration of the ensuing description and drawing.

SUMMARY

In accordance with the present invention a personal biofield vitalizer is worn around the neck during air travel to offset the adverse effects of air travel and consists of two parts which combine synergistically: a corona discharge air cleaner suspended on the chest which produces high-energy particles like ozone, nitric oxide, and free electrons which purify the air of airborne pathogens and pollution and increases the availability of electrical energy stored in the air, and a magnet at the base of the cervical spine which provides a magnetic field through the lungs and heart equivalent in strength to Earth's magnetic field at ground level so as to supplement the available magnetic energy in the body. This magnetic field also pulls stagnant energy out of the base of the neck to reduce the buildup of tension in the neck, and in combination with the air ionization, reduces sensitivity to crowds.

Figure 1:
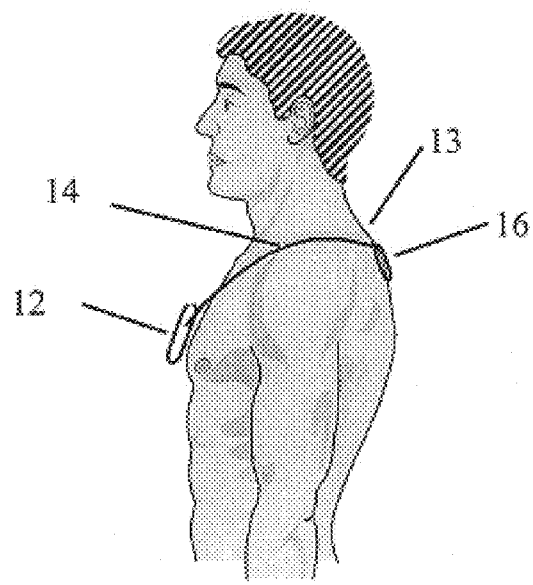
FIG. 1 shows an individual wearing a biofield vitalizer in accordance with my invention.
Figure 2:
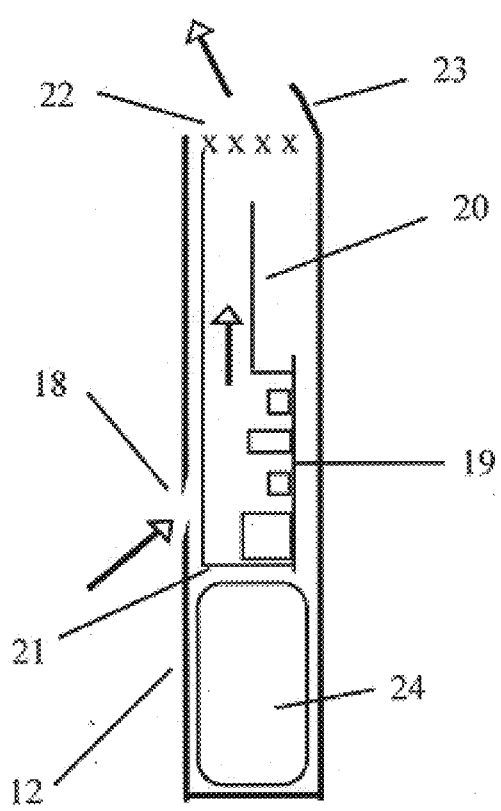
FIG. 2 shows an air purifier improved with air flow in accordance with my invention.
Figure 3:
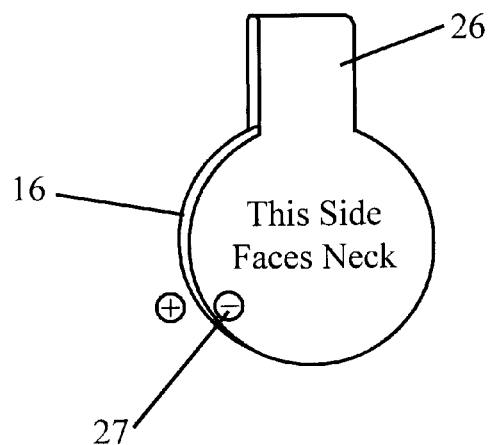
FIG. 3 shows a magnet of the biofield vitalizer in accordance with my invention.

Description—FIGS. 1 to 3—Biofield Vitalizer

FIG. 1 shows a biofield vitalizer in accordance with the invention. The vitalizer comprises a neck cord 14, a corona discharge air purifier 12, and a magnet 16. Neck cord 14 supports air purifier 12 over the chest and magnet 16 over the seventh cervical vertebrae of the neck of traveler 13 with the north or negative pole facing the neck. As long as the spine is vertical, gravity will pull the air purifier and magnet toward their proper positions.

FIG. 2 shows corona discharge air purifier 12, which is an improved version of the air purifier described in the above patent to Weinberg. It provides a corona discharge which produces free ions, ozone molecules, nitric oxide molecules, and other high energy, unstable molecules. These electrically energized molecules purify the air by reacting with airborne pathogens. They also surround the body and are absorbed by the pores and lungs and are assimilated to energize chemicals within the body like nitric oxide and other neuro transmitters, and many other energized chemicals which drive chemical reactions. The result is increased health, vitality, and immunity. This air purifier is manufactured by Wein Products, 115 West 25th Street, Los Angeles, Calif. 90007

The improvement over Weinberg results from the inclusion of air intake vents 18 on the front panel of the air purifier 12 through which air enters and passes over a grounded electrode wire 21 which causes a positive charge in the air. This charge creates an ionic attraction between the air and a negatively charged corona discharge electrode 20, toward which the charged air is drawn. As the air passes this electrode, it is purified, electrified, and charged negatively by an electronic circuit 19. It is then ionically attracted toward a grounded electrode grill 22, where it loses much of its charge and proceeds out of the unit past molded lip 23 which redirects the upward discharged air to flow more forward toward the passenger's nose. The resulting flow-through design reduces turbulence and air flow restrictions, increasing air flow through the unit. It also draws air from in front of and below the body, rather than drawing previously vitalized air from above the neck and face area, and delivers it more directly to the traveler's nose. These factors increase the flow of purified, vitalized air delivered to the passenger without increasing energy consumption of the air purifier. Alternatively, the power draw of the purifier can be reduced to produce the same air flow and reduced power draw for extended life of a battery 24. Increasing unprocessed air flow through the purifier also reduces the concentration of ozone, reducing chance of irritation of nasal tissues.

FIG. 3 shows magnet 16 supported by means of attachment strip 26 of laminated plastic which extends the magnet downward from the position of the neck cord, positioning the magnet optimally over the lower cervical spine. In the initial experiments, a 25 mm diameter, 3 mm thick ceramic barium ferrite disc magnet was used. The magnet was charged so that one face was the positive pole and the opposite face (adjacent to the user) was the negative pole. (Definition: the "negative pole" of a magnet matches the polarity of the "north" pole of Earth and is equivalent to the "south" or "south seeking" pole of a compass. To avoid this confusing nomenclature I have used the term "negative pole".)

While this magnet configuration provided the 0.4 gauss field strength at the center of the chest required to match Earth's field strength, it also created a high field strength at the base of the cervical spine. As described above, this drew complaints from highly sensitive individuals, and led to an important discovery, that a magnet at the base of the neck, in conjunction with the air filter, alters the body's biofield, reducing psychic sensitivity. Through experimentation, I arrived at the final design, a flexible barium ferrite magnet, 40 mm diameter and 2 mm thick, made of barium ferrite mixed with a flexible plastic material, the sort of magnet commonly found on refrigerators. Though this magnet is much weaker near its surface, its larger diameter provides the same field strength at the center of the chest, 100 to 150 mm away. Highly sensitive individuals found this magnet design to be both comfortable and effective at reducing their sensitivity to proximity to crowds.

Operation of the Biofield Vitalizer

The air purifier consumes about 75 milliwatts and produces ozone at a concentration of about 0.04 ppm, within the limit that OSHA has established for ozone exposure. This supplementation of electrically energized particles is important in an enclosed space like a plane because the crowd of passengers quickly consumes the available supply of these particles from the air. In addition, the ambient cabin air passes through metal heating and air conditioning coils which ground much of the available energy of such particles brought in from the outside. To compound the problem, up to 90% of the air is recycled, and thus, already depleted of its electrically energized particles. Thus, a principal reason that people are exhausted after a long trip is that they are not supplied with the electrically energized particles which they need for normal metabolic functioning and a principal reason the biofield vitalizer eliminates these symptoms.

The magnet is strategically placed over the lower cervical spine to serve three purposes. First, the magnet creates a magnetic field through the lungs and the heart, the two parts of the body which have significant physical movement while the passenger sits so that bodily tissue and blood moving through the magnetic field become magnetically charged. This is important during air travel because the jet cabin is far away from the surface of Earth, greatly reducing the strength of Earth's magnetic field within the cabin, and the electrically conducting shell of the airliner further reduces the magnetic field available within the craft.

People need magnetic substance within their bodies for a wide variety of normal functions. When a magnetic field is not available, problems often develop, such as those identified within the area of traditional Chinese medicine as "Yin deficiency" including rising heat, nausea, and anxiety, often to the point of panic. These symptoms are effectively treated with Chinese herbs that strengthen Yin. My experiments have shown that providing of a magnetic field through the lungs relieves these symptoms during air travel in people with Yin deficiency symptoms. Thus, providing a magnetic field to the body during air travel makes the trip more comfortable, particularly for those who tend to panic or become uncomfortable whenever they fly.

A second benefit of the magnet is that the negative pole of the magnet faces the neck, and pulls pain and tension from that area, relieving neck tension, a common complaint on long plane flights.

Third, the magnet, placed at the base of the cervical spine apparently constricts the biofield which surrounds the body because many people claiming to have psychic or clairvoyant ability complained that the first prototypes of the biofield vitalizer made them uncomfortable and that their clairvoyant abilities were inhibited by this device.

Highly sensitive people were very pleased with the revised product because, while they were comfortable wearing it, they found that it still inhibited their sensitivity. Thus, they can wear it whenever they want to switch their psychic sensitivity off in crowded situations. This includes not only airplanes, but also busy stores and restaurants and intense personal conversations, and even phone conversations with emotionally distressed or angry people.

Experiments also revealed that the magnet or air purifier by itself does not constrict the field and reduce psychic sensitivity nearly as well as the synergistic effect of the magnet combined with the air purifier. Also, this field constriction requires that the magnet be placed over the seventh cervical vertebrae. If it is moved a few centimeters from this point, its effect decreases considerably. This phenomenon is believed to be associated with a structure identified in Indian and western metaphysical literature as the throat chakra, which is described as an important sensory organ for higher sense perception. The biofield vitalizer is so designed that, when it is worn with the magnet at the back of the neck, it is positioned right at this desired point. This technique—inhibition of sensitivity—is also applicable to other areas of the body such as the first lumbar vertebra which corresponds to the solar plexus chakra.

The electric air ionization and the magnetic field supplementation work synergistically. From the standpoint of traditional Chinese medicine a person who is low on Yin, the cooling, magnetic bonding aspect of the biofield, is unable to assimilate and hold onto the electrical, Yang aspect. This loss of ability to hold the Yang allows the Yang to rise and is the cause of the sensations of heat and anxiety experienced by many during air travel. My research showed that, while a magnet supplements the magnetic field surrounding air travelers and thus increases their electrical conductivity, it does not relieve their discomfort because they are still deficient on electrical ionization. In a similar way, just the electrical supplementation does not relieve their symptoms because they do not have the magnetic substance with which to grasp the electrical. Together, electrical and magnetic supplementation provide relief from the symptoms of anxiety, rising heat, and nausea, usually within just three or four minutes of putting on the unit, as the magnet allows the passengers to collect Yin magnetic substance, so that they can assimilate the Yang electrical ionization. Thus the combination of the electric and magnetic field supplementation is truly synergistic in that it provides far greater benefit than would be expected from the sum of their individual benefits.

Figure 4:
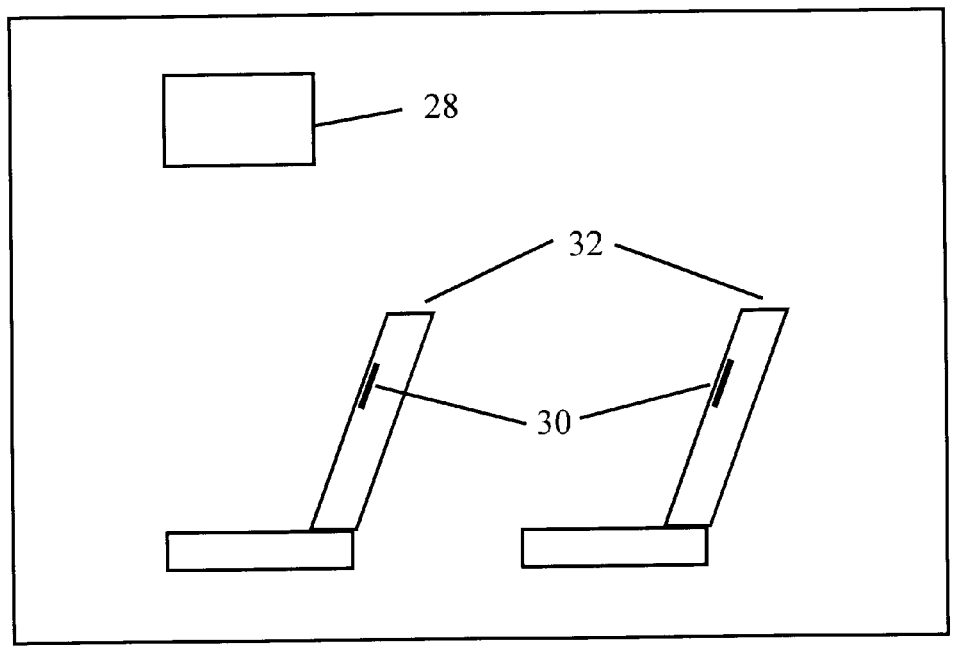
FIG. 4 shows the biofield vitalizer incorporated into airplane cabin in accordance with my invention.

Description—FIG. 4—Airplane Equipped with Biofield Vitalizer

FIG. 4 shows a configuration where the biofield vitalizer is installed in an airplane. While an individual can choose to wear a personal vitalizer, an airline can choose to provide a similar benefit to all passengers. In this configuration, several of a more powerful version of the corona discharge air purifier 28 are attached to the cabin or in the air conditioning ductwork. Whereas the personal air purifier consumes a power of about 75 milliwatts, this larger unit consumes about 5 watts and produces about 50 times the ionized air output. Eight should be provided in a 747 jumbo jet, two in each cabin. Also a magnet 30 is inserted in each seat back 32. A 150 mm long, 30 mm wide strip magnet made of 1 mm thick low strength flexible barium ferrite magnetic material, mounted along the center of the seat back, provides an adequate magnetic field through the lungs of passengers and accommodates people of varying sizes. With this configuration, all the passengers on a flight can benefit from the electric and magnetic supplementation and air purification of the biofield vitalizer. However, for the added benefit of reduced sensitivity provided by the precisely located magnet over the lower cervical spine, a magnet must be worn on the body, as shown in FIG. 1.

This configuration is also applicable to automobiles to overcome the magnetic depletion caused by the steel body of the automobile and the electric depletion from the polluted air found along most roadways. Not only will this help health, vitality, and mood, but it will also reduce the growing tendency of "road rage". Thus, car manufacturers will produce a safer car and safer roads if they include the biofield vitalizer into every car they produce.

Another important application provides improved health and vitality for domesticated animals. Dairy and beef cows, pigs and poultry require ever increasing dosages of antibiotics to fight off disease, and yet disease is a growing problem which hurts economically, with the high cost of antibiotics, the high death rate, and rejection of diseased animals. A big part of the problem is the same as occurs in airplanes: crowding together with high airborne pollutants and reduced availability of magnetic and electrical supplementation. The reduced magnetic supplementation is due to the steel construction of structures including buildings, cages, and stalls. This means that the magnetic field of Earth is shunted around the animals through the steel. Also, the air conditioning systems reduce the available air ionization by grounding it in the heating and cooling coils, ductwork, and grills. Also, the high level of pollution from gasses from animal waste absorbs most of the available electrical ionization, as do the animals themselves.

Living in crowded circumstances these steel, air conditioned buildings is much like flying on a modem jetliner. The animals are exhausted and irritable at the end of every day. Their immune systems are depleted, and thus, they catch disease easily. And when they get sick and contaminate the air with bacteria and viruses, the unionized air spreads these contaminants easily to other animals.

The electrical ionization can be provided at the individual animal's cage or stall, though it will be more economical if provided at the air conditioning inlet or at central locations in the room. The magnetic supplementation will be provided at the cage or stall. While there are many ways to provide a magnetic field such as hanging magnets around the animals' necks and the traditional "cow magnets" which are swallowed by cows to aid in digestion, the following is the preferred embodiment at this time. The magnetic material is fabricated from one millimeter thick low strength flexible barium ferrite material laminated to thin sheet stainless steel or other durable, non ferromagnetic material. This material, in two inch squares, is attached to the inside of chickens' cages and in six inch squares is attached to the inside walls of stalls for cows. It must be inside of all metal walls. The magnet is magnetized with one side positive and the other side, facing the animal, negative. It is placed in a position where the animal can easily stand or brush against it.

In this way, the animal gains all the magnetic supplementation it requires and is thus able to assimilate the electrical ionization provided by the ionizer. The biofield vitalizer, in a configuration suitable for animals, is a highly economical answer which will save on drugs and animals lost to disease. It will provide more vital, and thus healthier, faster growing, more reproductive animals, and better tasting meat. It will also provide more profitable dairy and poultry businesses and positive public relations from less disease in livestock.

Safety and Efficacy

The biofield vitalizer has been used for six months with over 1000 individuals, and has received high praise for efficacy in reducing discomfort and exhaustion during air travel and relieving symptoms of environmental sensitivity. I have received no complaints of medical problems arising from its use. It meets OSHA requirements of not exceeding 0.1 ppm of ozone at 150 mm from its grounded electrode grill 22.

CONCLUSIONS, RAMIFICATIONS, AND SCOPE

The biofield vitalizer provides many benefits. Most importantly, it solves the problems of air travel discomfort and exhaustion induced by low magnetic field, electrically depleted air and airborne pathogens. It does this by purifying the air of pathogens, surrounding the heart and lungs with a magnetic field of strength similar to that of Earth at ground level, and surrounding the body with electrically charged air molecules like ozone, nitric oxide and free ions. Additional benefits include pulling out the tension which builds up at the base of the neck and reduction of sensitivity of people who are hypersensitive to crowded situations.

This device can be applied wherever magnetic or electric fields are reduced, such as in steel-framed air conditioned buildings which reduce both magnetic and electric availability. It can be used in polluted environments or by people who have environmental hypersensitivity because it both cleans the local environment and strengthens both the electric and magnetic aspects of the individual's bio-electromagnetic field, strengthening resistance to environmental irritants. The biofield vitalizer can also be used in all kinds of vehicles, where the metal, (and particularly steel) construction shunts Earth's magnetic currents around the interior, and where the ventilation system further depletes the electric vitality of the already depleted air which is present along roadways. Supplementation of the magnetic field surrounding the driver reduces Yin deficiency symptoms like irritation and anger, thus reducing roadway aggression, dubbed "road rage". When insurance companies discover that electromagnetic field supplementation reduces fatigue and irritability and increases alertness, they may offer insurance rate discounts for safety when cars are equipped with biofield vitalizers.

An additional application is in hospitals where patients are generally low on electric and magnetic vitality because of illness and building construction. Also, hospital employees can wear the vitalizer to prevent "nurse's burnout" which is, to a large extent, caused by depleted electric and magnetic vitality, exposure to pathogens and chemicals like alcohol, and close proximity to other people. The biofield vitalizer can also be used for all kinds of animals and plants. Steel framed hot houses suffer from vitality depletion and will benefit from the electrical and magnetic supplementation of the biofield vitalizer.

Other ramifications include packaging the magnet within the air purifier to simplify the package or to add other components to the air purifier such as various resonant circuits or crystals so as to further vitalize or harmonize the human body. The air purifier can be reconfigured to be long and narrow, orienting the batteries vertically. This adds to the stability of the unit, so that it is more likely to remain optimally positioned. This provides a more square shape of ionization chamber discharge, which provides a more focused, less restricted stream of purified and ionized air directed toward the nose. The magnet can be square or any other shape, and can be made larger in diameter and thinner or made in the shape of an annulus to provide the required field strength at the center of the chest while providing a lower strength at the spine.

Thus, the scope of the invention should be determined by the appended claims and their legal equivalents, rather than by the examples given.

I claim:

1. An environmental conditioning device for use with a living body comprising:

an air ionizing component for supplying ionized air to the living body, and a magnetic field production component disposed in close proximity to the living body wherein said magnetic field production component produces a magnetic field strength of approximately 0.4 gauss, the average magnetic field strength at the surface of the Earth, within the living body.

2. The environmental conditioning device of claim 1 wherein said magnetic field production component has a negative pole and wherein said negative pole is positioned facing the living body.

3. The environmental conditioning device of claim 1 wherein the living body has a cervical spine having a base and wherein said magnetic field production component is positioned at the base of the cervical spine.

4. The environmental conditioning device of claim 1 wherein said magnetic field production component has a diameter of greater than 25 mm.

5. The environmental conditioning device of claim 1 wherein said magnetic field production component is formed from a flexible barium ferrite magnet approximately 40 mm in diameter and 2 mm thick.

6. The environmental conditioning device of claim 1 wherein said air ionizing component comprises a housing having an opening through which ionized air is directed and wherein said opening has a lip for redirecting the air in an upward direction.

7. The environmental conditioning device of claim 1 wherein said air ionizing component comprises a housing, said housing having a first opening through which ambient air is drawn into an ionization chamber and a second opening through which ionized air is directed.

8. An environmental conditioning device for use with a living body comprising:

an air ionizing component for supplying ionized air to the living body, and a magnetic field production component disposed in close proximity to the living body wherein said magnetic field production component produces a maximum magnetic field strength of less than 100 gauss within the body.

9. The environmental conditioning device of claim 8 wherein said magnetic field production component has a negative pole and wherein said negative pole is positioned facing the living body.

10. The environmental conditioning device of claim 8 wherein the living body has a cervical spine having a base and wherein said magnetic field production component is positioned at the base of the cervical spine.

11. The environmental conditioning device of claim 8 wherein said magnetic field production component has a diameter of greater than 25 mm.

12. The environmental conditioning device of claim 8 wherein said magnetic field production component is formed from a flexible barium ferrite magnet approximately 40 mm in diameter and 2 mm thick.

13. The environmental conditioning device of claim 8 wherein said air ionizing component comprises a housing having an opening through which ionized air is directed and wherein said opening has a lip for redirecting the air in an upward direction.

14. The environmental conditioning device of claim 8 wherein said air ionizing component comprises a housing, said housing having a first opening through which ambient air is drawn into an ionization chamber and a second opening through which ionized air is directed.

15. An environmental conditioning device for use with a living body comprising:

an air ionizing component for supplying ionized air to the living body, and a magnetic field production component disposed in close proximity to the living body wherein said magnetic field production component produces a minimum magnetic field strength of approximately 0.4 gauss.

* * * * *